(12) United States Patent
Fogher

(10) Patent No.: US 8,563,827 B2
(45) Date of Patent: Oct. 22, 2013

(54) MUTAGENIZED TOBACCO PLANT AS SEED CULTURE FOR THE PRODUCTION OF OIL FOR ENERGETIC, INDUSTRIAL AND ALIMENTARY USES

(75) Inventor: Corrado Fogher, Casalmaggiore (IT)

(73) Assignee: AEP-Advanced Ecopower Patents S.A., Locarno (CH)

( * ) Notice: Subject to any disclaimer, the term of this patent is extended or adjusted under 35 U.S.C. 154(b) by 643 days.

(21) Appl. No.: 12/531,202

(22) PCT Filed: Aug. 27, 2007

(86) PCT No.: PCT/IB2007/053412
§ 371 (c)(1),
(2), (4) Date: Nov. 12, 2009

(87) PCT Pub. No.: WO2008/110876
PCT Pub. Date: Sep. 18, 2008

(65) Prior Publication Data
US 2010/0058655 A1    Mar. 11, 2010

(30) Foreign Application Priority Data
Mar. 14, 2007    (IT) ............................ RM2007A0129

(51) Int. Cl.
| | |
|---|---|
| *A01H 1/04* | (2006.01) |
| *A01H 1/06* | (2006.01) |
| *A01H 5/00* | (2006.01) |
| *A01H 5/10* | (2006.01) |
| *C12N 5/04* | (2006.01) |
| *C12N 5/14* | (2006.01) |
| *C12N 15/00* | (2006.01) |
| *C12N 15/82* | (2006.01) |

(52) U.S. Cl.
USPC ........ 800/317.3; 800/270; 800/276; 800/278; 435/414; 435/419; 435/440; 435/468

(58) Field of Classification Search
None
See application file for complete search history.

(56) References Cited

U.S. PATENT DOCUMENTS

| | | | | |
|---|---|---|---|---|
| 4,592,762 A * | 6/1986 | Babu et al. | .................. | 48/197 R |
| 5,498,544 A * | 3/1996 | Gengenbach et al. | ...... | 435/320.1 |
| 6,730,832 B1 | 5/2004 | Dominguez et al. | | |
| 7,910,718 B2 * | 3/2011 | Simkin et al. | ................ | 536/24.1 |
| 8,237,014 B2 * | 8/2012 | Blaylock et al. | .............. | 800/278 |
| 2006/0288454 A1 * | 12/2006 | Sanz Molinero | ............. | 800/287 |

OTHER PUBLICATIONS

Giannelos et al, Industrial Crops and Products, vol. 16, pp. 1-9, 2002.*
Brown and Caligari, "An Introduction to Plant Breeding", 2008, Blackwell Publishing Ltd., chapter 8, selected passages.*
Choe et al, The Plant Journal, Jun. 2001, vol. 26, Issue 6, pp. 573-582.*
Anonymous "Burley (tobacco)" Wikipedia article, one page (last edited Sep. 2009).
Akehurst *Tobacco* London: Longman, pp. 90-92 (1968).
Avery "Structural responses to the practice of topping tobacco plants: A study of cell size, cell number, leaf size, and veinage of leaves at different levels on the stalk" Botanical Gazette 96:314-329 (1934) (abstract only).
Bailey "Dark tobacco sucker control" UK Cooperative Extension Service, AGR-154, two pages (issued Aug. 2007).
Gopinath et al. "The mode of gene action in flue-cured tobacco" Euphytica 16:293-299 (1967).
Matsuda & Sato "Studies on the breeding of varieties having low sucker productivity in tobacco (*Nicotiana tabacum* L.) I. Varietal differences in sucker-producing characteristics of tobacco" Japan J. Breed. 31:395-401 (1981).
Matsuda & Sato "Studies on the breeding of varieties having low sucker productivity in tobacco (*Nicotiana tabacum* L.) III. Inheritance of sucker productivity in two varietal crosses" Japan. J. Breed. 32:317-322 (1982).
Sisson "Tobacco breeding, genetics, and germplasm preservation" CRIS accession 0139007, eight pages (updated 2005).
Steinberg & Jeffrey "Comparison of pruning (topping, suckering) effects in normal and boron-deficient tobacco on relative growth and alkaloid content of leaf, stalk, and root" Plant and Soil 9:64-74 (1957) (abstract only).
Stephenson "Cultural and nutritional studies in tobacco production" CRIS accession 0193982, two pages (updated 2005).
Tajima et al. "Breeding of the low sucker productivity flue-cured tobacco variety, F66" Bull. Leaf Tobacco Res. Lab. 7:203-215 (1998) (abstract only).
Wernsman "Tobacco breeding and genetic investigations" CRIS accession 0189410, three pages (updated Jan. 2006).
Wilkinson et al. "Registration of 'VA 119' tobacco" Crop Science 46:1392 (May-Jun. 2006).
Int'l Search Report for PCT/IB2007/053412, five pages (Apr. 4, 2008).
Written Opinion for PCT/IB2007/053412, eight pages (Apr. 4, 2008).
Kodym & Afza "Physical and chemical mutagenesis" *Methods in Molecular Biology*, vol. 236, pp. 189-204 (2003).
Madoka et al. "Chloroplast transformation with modified *accD* operon increases acetyl-CoA carboxylase and causes extension of leaf longevity and increase in seed yield in tobacco" *Plant and Cell Physiology*, vol. 43, No. 12, pp. 1518-1525 (2002).

(Continued)

*Primary Examiner* — Eileen B O Hara
(74) *Attorney, Agent, or Firm* — Nixon & Vanderhye PC

(57) ABSTRACT

The present invention relates to the development of tobacco plants, modified through mutagenesis techniques, interspecific hybridisation followed by poliploidisation and recombinant DNA technologies, characterised by the fact of being capable of producing a very high amount of seeds and their use for the production of oil for energetic and industrial scopes, such as combustion oil, biodiesel and lubricating oil, and for animal and human alimentation.

17 Claims, 2 Drawing Sheets

(56) References Cited

OTHER PUBLICATIONS

Figure 1:
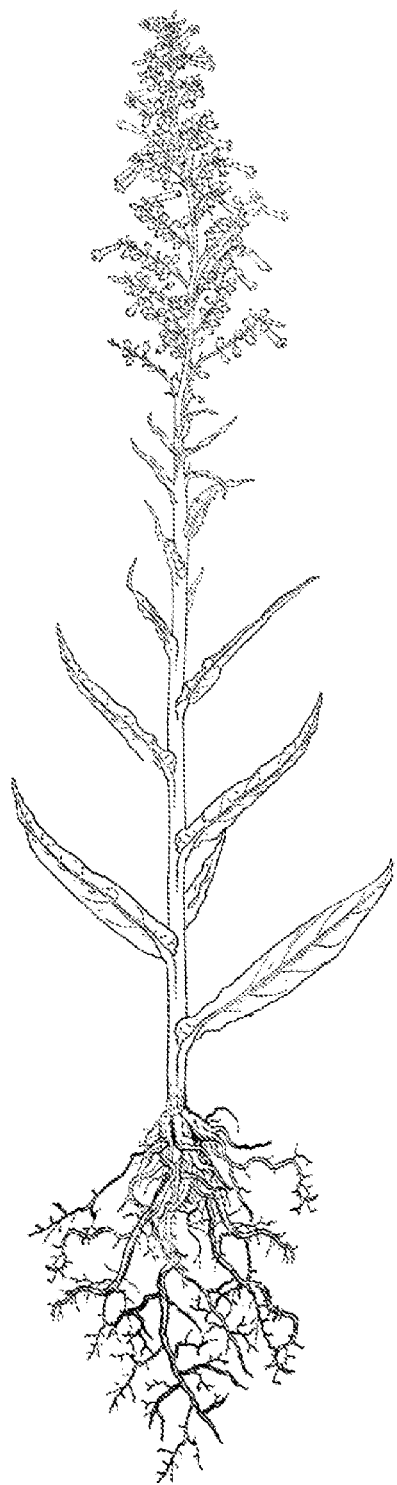

Patel et al. "Production potential and quality aspects of tobacco seed oil" *Tobacco Research*, vol. 24, No. 1, pp. 44-49 (1998).

Usta "Use of tobacco seed oil methyl ester in a turbocharged indirect injection diesel engine" *BioMass and BioEnergy*, vol. 28, No. 1, pp. 77-86 (Jan. 2005).

Veljkovic et al. "Biodiesel production from tobacco (*Nicotiana tabacum* L.) seed oil with a high content of free fatty acids" *Fuel*, vol. 85, No. 17-18, pp. 2671-2675 (Dec. 2006).

Bondioli, Fatty acid composition of tobacco seed oil, report 10LA01350, one page (May 2010).

Rovelini, Fatty acid composition of tobacco seed oil, report 11LA01742, two pages (May 2011).

Rovelini, Fatty acid composition of tobacco seed oil, report 11LA01745, two pages (May 2011).

Giannelos et al. "Tobacco seed oil as an alternative diesel fuel: Physical and chemical properties" *Industrial Crops and Products*, vol. 16, No. 1, pp. 1-9 (2002).

International Standard "Petroleum products—Determination of pour point" *ISO 3016*, $2^{nd}$ Ed., pp. 1-6 (1995).

Stanisavljevic et al. "Comparison of techniques for the extraction of tobacco seed oil" *Eur. J. Lipid Sci. Technol.*, vol. 111, No. 5, pp. 513-518 (May 2009).

\* cited by examiner

MUTAGENIZED TOBACCO PLANT AS SEED CULTURE FOR THE PRODUCTION OF OIL FOR ENERGETIC, INDUSTRIAL AND ALIMENTARY USES

This application is a U.S. national phase under 35 U.S.C. 371 of International Application No. PCT/IB2007/053412, filed 27 Aug. 2007, which designated the U.S. and claims priority to IT RM2007A000129, filed 14 Mar. 2007; the entire contents of each of which are hereby incorporated by reference.

BACKGROUND ART

Tobacco has been cultured, in the beginnings, as an ornamental and as a medical plant, imposing itself subsequently as an essentially luxury good getting into human culture and modifying human customs and habits.

Tobacco has, amongst the agricultural plants, a position that is not comparable with other plant crops and presents certain peculiarities such as:

1. it is one of the few plants marketed only for its leaves;
 2. it is the major non-alimentary plant in the world with a production extension higher than four million hectares in the whole world;
 3. in many countries it is a very important instrument for economical and financial politic;
 4. its consumption is based on the transformation of the leaves into smoking products, inhaling powders and chewable products;
 5. considering its narcotic substance characteristics and its dangerousness for human health, there have always been attempts aimed to forbid its use and hence its production.

The evolution of the *Nicotiana* genus into different habitats, initially through natural selection and poliploidisation and, later on, through human-driven selection, has brought to the appearance of a vast range of kinds, all selected on the basis of the leaf properties being the leaf considered as the only valuable part of the plant.

Recently, alternative uses of tobacco have been indicated in addition to the above-listed ones:

1. the production of alimentary proteins through purification thereof from leaves (Long R. C. 1979. Tobacco production for protein. Project n. 03245. North Carolina State university, Raleigh N.C.);
 2. the extraction of pharmacologically useful active ingredients normally present in the leaves (Baraldi M. et al. 2004. Presenza di sostanze Benzodiazepino-simili in estratti di foglie di tabacco (*Nicotiana tabacum*). Atti Ist. Sper. Tab., 23 Aprile, Roma, pp. 45-52);
 3. the production of recombinant proteins expressed in the leaves or in the seeds of genetically modified plants (Twyman et al. 2003. Molecular farming in plants: host systems and expression technology. Trends Biotechnol. 21:570-578).

The tobacco plant presents a very large leaf area, a small inflorescence and a ratio aerial part:roots that is the highest observed among agricultural plants (Went, 1957. The experimental control of plant growth. pp. 343. Chronica Botanica, Waltham, Mass.).

Taking into account the economic relevance exerted by tobacco's cultivation, notwithstanding the alarming increase of tabagism amongst the youngest, Europe provides grants for its cultivation giving rise to perplexity both of economical and ethical nature.

The European Commission on its internet site (www.e-c.europa.eu/agriculture/publi/fact/tobacco) affirms: "there are no economically valid alternatives to this culture that does not use good soils. The incentives to tobacco's culture permits the survival of the rural tissue and produces an industrial activity that contributes to the survival of regions menaced by desertification".

The negative consequences, in environmental terms, of the use of fossil combustibles and the limited availability of petroleum, require the search of new energetic sources. Amongst these, biofuels are the best choice in a future perspective due to their renewability.

Considering bio fuels of agricultural origin, up to date, the attention has focused on the production of bioethanol starting form simple (i.e. saccharose) or complex (i.e. cellulose) sugar producing plants. Model plants for such production has been identified in sugar cane, corn, wheat, potato, tapioca, sugar beet, barley, sorghum etc. The development of cultures aiming to the maximisation of the production of biomass to be transformed in ethanol through fermentation processes or for the production of biofuels or gas through gasification may have the same scope. Alternatively, the state of the art aims to the production of fuel oil and biodiesel starting form oleaginous or non oleaginous species but rich in oil such as soybean, sunflower, rape, peanut, flax, corn, sesame, palm, palm-kernel, coconut, ricinus etc.

The choice of the ideal species for the production of biofuels shall relate on the fulfilment of requirements such as:

1. determining a net energetic gain in the difference between culture's input and output, comprising in the said calculation the energetic costs for the production of the agricultural machinery and for the processing for the extraction and transformation/purification of the oil;
 2. determining environmental benefits deriving from the supportability of the agricultural production, decrease of the $CO_2$ and particulate matter (e.g. PM-10) emission after combustion and limited use of agrochemicals such as pesticides herbicides and fertilizers;
 3. being economically competitive and, possibly, determining social benefits that may increase the system's economy, e.g. by lowering indirect costs on the sanitary system, considering also that the fossil energy used at presents imposes environmental costs that are usually not in the cost determination; a bio fuel shall envisage benefits both on the cost competitiveness side and on the environmental side;
 4. being available in large quantities without decreasing the alimentary availability; the use of agricultural plants traditionally used for food production does not reasonably allow their use for the production of bio fuels without determining a reduction of the food sources deriving from said plants hence increasing the costs of the raw materials;
 5. the plant culture from which it derives shall possibly concern marginal lands that are not likely to be used for alternative cultures.

In the state of the art the plants taken into account for oil production are: soybean (*Glycine max*), sunflower (*Helianthus annuus*), rape (*Brassica napus*), peanut (*Arachis hypogaea*), ricinus (*Ricinus communis*), flax (*Linum usitatissimum*), corn (*Zea mais*), sesamus (*Sesamum indicum*), palm (fruit, Aracaceae), palm-kernel (seed, Aracaceae), copra (coconut, *Cocos nucifera*), safflower (*Carthamus tinctorius*), olive (*Olea europea*), cotton (*Gossypium* sp.), acajou (*Anacardium occidentale*), hemp (*Cannabis sativa*), poppy (*Papavers* sp.), mustard (*Brassica* sp.), grape (*Vitis* sp.), apricot (*Prunus armeniaca*), pine (*Pinus* sp.), argan (*Argania spinosa*), avocado (*Persea americana*), almond (*Prunus amygdalus*), hazelnut (*Corylus avellana*), nut (*Juglans regia*), neem (*Azadirachfa indica*), niger (*Guizotia abyssinica*), jojoba (*Simmondsia chinensis*), rice (*Oryza sativa*), pumpkin (*Cucurbita* sp.), crambe (*Crambe abyssinica*).

On the contrary, in the prior art, tobacco has always been considered as an agricultural plant apt for the production of leaves.

The only three publications in literature, listed below, suggesting further uses for tobacco, take into account the present tobacco varieties, that have been selected for the production of leaves, as a source of the seed by-product for oil extraction.

In particular Giannelos et al. (Tobacco seed oil as an alternative diesel fuel: physical and chemical properties. Industrial Crops and Products, 2002, 16:1-9) declaring that "the seed is a by-product of the leaf production in Greece" suggest the possibility of using said seeds for the production of fuels describing methods for the extraction of oil form tobacco seeds that uses solvents, indicating, however, that the oil extracted from tobacco may not be used as such as biodiesel due the high iodine value in it.

Usta N. (Use of tobacco seed oil methyl ester in a turbocharged indirect injection diesel engine. Biomass and Bioenergy, 2005, 28:77-86) declares that tobacco seed oil is a by-product of the world production of leaves, estimates the worldwide production of seed deriving from tobacco's cultivation for leaves and describes the oil extraction from seed through the use of solvents.

Finally, Patel et al. (Production potential and quality aspects of tobacco seed oil. Tobacco Research, 1998, 24:44-49) estimate the production of tobacco seed as a by-product of leaves in India equal to 1,171 kg/ha with a content of oil of the 38% by weight and describe its extraction by the use of solvents.

The technological processes for oil extraction comprise mechanical (pressure) and chemical (solvents) techniques. In practice, the two systems are often combined. In general the mechanical extraction is carried out on seeds containing more than 20% of fat material (e.g. rape and sunflower) wherein the seeds dimensions are favourable for the pressing technique. Tobacco seed, by way of example, due to its very tiny dimensions, is subject to oil extraction by chemical treatments.

Generally, the possibility of extracting oil mechanically, facilitates the direct extraction in the seed production sites, hence also at the farm's level, with small plants.

For lower quantities of fat material chemical extraction is used, and can be applied also to the oilcake, leftover of the mechanical extraction, in order to recover the remaining 6-12% of oil left after the mechanical treatment. The oils extracted by the use of solvents (e.g. hexane) prior to commercialisation for alimentary uses, require a refinement step. The main product of the extraction process is crude oil; the mechanical extraction further produces the protein oilcake whereas the chemical one produces flour. The latter, used in animal feeding, weights in a critical way upon the production and processing of oily seeds economy.

In certain cases the production is bound to the protein flour request (e.g. soybean). The crude oil may subsequently be rectified with a series of physicochemical treatments (e.g. pH adjustment, filtration, degumming, discolouration, etc.) depending on the intended use.

The mass balance of the entire process varies from species to species, by way of example considering a content in oil of 42% for the sunflower seeds, for a ton of seeds (that are the main product) 2.6 by-product (biomass) tons are considered, with a production of 420 kgs of crude oil, 580 kgs of oilcake, obtaining a final production of 390 kgs of refined oil and 30 kgs of process residuals. Taking into account that the average yield of sunflower seeds is about 2.6 t/ha (+/−15%) it can be calculated that the yield/hectare of oil is equal to about one ton. This relation is valid also for other species, in particular for rape, depending on the percentage in oil. Vegetable oils may be used directly as fuel oils for heat production (ovens or boilers) or mechanic energy production (engines), utilizing their gross calorific value that is about 8,500 kcal/kg or, after transesterification, transformed as biodiesel.

The use of vegetable oils in boilers may be carried out with conventional burners by substituting the industrial or the heating diesel oil with vegetable oil. This kind of solution appears quite interesting due to the fact that: (i) the price of substituted fossil fuel is often quite similar to the one of the automotive diesel oil and is subject to high excise duties; (ii) the use of oil in boilers requires the organisation of a very simple agroenergetic thread that can end directly in the rural environment, where the fuel producers and the fuel users can be located very near to each other or can even correspond. The higher or lower easiness of the oil extraction process is another important aspect to take into account when an local use of the bio fuel is envisaged. The production economy and the more or less favourable energetic balance will depend mainly on the production per hectare of fuel oil.

The use of vegetable oils in diesel engines requires, on the other hand, a chemical process of transesterification with methanol and a certain fatty acid composition, which may be summarised in a iodine value that has to be equal or lower than 120. Vegetable oils are also often used for alimentary scopes. Depending on the plant, the productions can be mainly directed to alimentary or energetic scopes, or both.

On the light of the above mentioned problems, it would be highly desirable to recycle tobacco's industry for ecological scopes and harmless for human beings.

The identification of an alternative and economically valid use of tobacco does hence constitute a clear worldwide economically interesting topic.

SUMMARY OF THE INVENTION

The present invention discloses the realisation of tobacco plants suitable for a very high production of a particular component of the plant: the seed. Said plants have been realized through somatic in vitro, chemical or physical mutagenesis techniques and/or by interspecific crossbreeding and subsequent chromosomal duplication. Said plants are optionally further modified by genetic engineering techniques. The tobacco's plant selection in the state of the art has always been directed towards the leaf as final product, the focusing of the attention and, hence, the plants selection for the maximisation of the seeds production has never been suggested before and allows the use of tobacco in order to maximise the production of seed to the detriment of the leaf production.

It has been surprisingly found that the selection of tobacco plants, carried out using non biological techniques of chemical, physical and somatic in vitro mutagenesis techniques, of crossing also between different species, followed by the induction of amphidiploids and, optionally by recombinant DNA techniques, has allowed to obtain tobacco plants presenting the following characteristics:

they present the ideal characteristics for the transformation of the tobacco agricultural plant from a plant of leaf production to a plant for seed production;

they have the capability of producing seeds up to values of from 20 quintals/hectare, to 50 quintals/hectare, or to 70 quintals/hectare, or even to 90 quintals/hectare with the possibility of further improvements in the yield of seed/hectare;

they present a seed oil content up to 38% of the seed weight, or up to 40%, or up to 48%, or up to 52% or up to 58% or even up to 60%;

they have a low necessity of agronomical inputs for the defence against parasites and weeds.

Furthermore, completely unexpectedly, due to the small dimensions of the tobacco seed that is, amongst the cultivated plants, one of the smallest seeds, the present invention shows that it is possible to extract oil from the seed by pressing reaching extraction yields that are about the 80% of the total oil present in the seed, about the 90% of the total oil present in the seed or even about 95% of the total oil present in the seed, thus granting the possibility of carrying out the extraction also in small plants for farms use.

Hence, object of the invention are tobacco plants that are mutagenised and/or obtained by interspecific crossing followed by diploidisation and selection, characterised in that they produce a seed quantity equal to at least 20 quintals/hectare, said plants optionally further modified by genetic engineering, the use of said plants for the production of seeds, for the manufacturing of oil and derivatives thereof, the use of said plants for the production of biomass for the biochemical or thermo chemical conversion, the method of producing and selecting said plants, the seeds of said plants and their use for the manufacturing of oil and derivatives thereof, the oil deriving from said seeds, the biodiesel obtained from said seeds, food supplement derived from tobacco, solid fuels comprising the oilcake resulting from pressing tobacco seeds, the method for oil extraction from tobacco seeds by pressing.

DETAILED DESCRIPTION OF THE FIGURES

FIG. 1. General characteristics of the tobacco plant realised through chemical mutagenesis, intra and interspecific crossing, poliploidisation, selection, induction of somaclonal variability, genetic transformation, aimed to maximise the seed production per surface unit, with a high oil content and having characteristics suitable for the use as energetic source, for industrial uses and for human and animal nutrition. Principal induced and selected characteristics: deep and wide radical apparatus; thin and erected lanceolate leaves; robust stalk at the basis with long internodes; cob-like inflorescence compact, wide or columned; short pedicellate, non-dehiscent capsules, di- or multi-valve, straight apex, with at least 5000 seeds/capsule; oval or elliptical seeds of a length >than 1 mm; plant height between 50 and 120 cm, insect resistance, herbicides resistance, fungi resistance, drought resistance, variable ratio among the fatty acids components.

Figure 2:
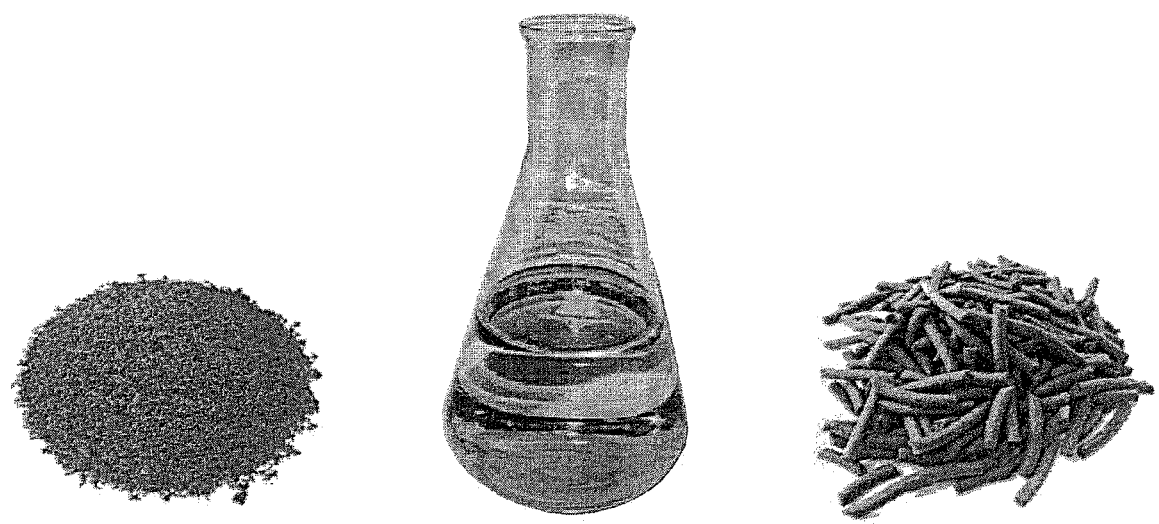

FIG. 2. Example of the product oil and oilcake obtained from tobacco seed by pressing with a screw-press mod. Komet (IBG). After pressing the oil has been filtered in paper and presents high limpidity characteristics.

DETAILED DESCRIPTION OF THE INVENTION

The present invention, hence, relates to the realization of plants of the *Nicotiana* genus, as ideal plants for the production of seed from which fuel oil, biodiesel, proteins, oil for zootechnical use, for industrial use, for human alimentary use is obtained.

The varieties of the *Nicotiana* genus that may be used as parental plants for the carrying out of the plants of the invention may be, by way of example, comprised among the following species: *N. tabacum, N. rustica, N. glauca, N. paniculata, N. knightiana, N. solanifolia, N. benavidesii, N. cordifolia, N. raimondii, N. thyrsiflora, N. tomentosa, N. tomentosiformis, N. otophora, N. setchellii, N. glutinosa, N. ondulata, N. arentsii, N. wigandioides, N. trigonophylla, N. palmeri, N. sylvestris, N. langsdorffii, N. alata, N. forgetiana, N. bonariensis, N. longiflora, N. plumbaginifolia, N. repanda, N. stocktonii, N. nesophila, N. moctiflora, N. tomentosiformis, N. otophora, N. setchellii, N. glutinosa, N. petunioides, N. acaulis, N. ameghinoi, N. acuminata, N. pauciflora, N. attenuata, N. miersii, N. corymbosa, N. linearis, N. spegazinii, N. bigelovii, N. clevelandii, N. nudicaulis, N. maritima, N. velutina, N. gossei, N. excelsior, N. megalosiphon, N. exigua, N. goodspeedii, N. ingulba, N. stenocarpa, N. occidentalis, N. rotundifolia, N. debneyi, N. benthamiana, N. fragrans, N. suaveolens, N. obtusifolia.*

According to the present invention, the plant will be achieved by means of mutagenesis techniques that will allow to develop plants capable of producing a quantity of seeds higher than the average with respect to the starting individuals. Mutagenesis may be induced by standard chemical and/or physical treatment techniques of tobacco seeds, or also by in vitro culture for the induction of somaclonal mutants. The higher production of seed may be obtained also by generating hybrid plants produced by interspecific crossing followed by diploidisation of the chromosome set (in order to obviate to the sterility events displayed by interspecific hybrids) by chemical treatment with colchicine. The plants produced by interspecific crossing may be further mutagenised by chemical and/or physical standard techniques.

Once the mutants are obtained, they will be selected for the seed production character, so to isolate and select plants producing at least 20 quintals of seed per culture hectare.

According to the present invention, the plant will be hence realised starting from seeds produced by:

1. crossing between individuals of the same species or
2. crossing between individuals of different species having the same chromosome number (e.g. *N. tabacum*×*N. clevelandii*) as such or wherein said crossing is followed by embryo culture methods and poliploids induction by treating with the mutagen colchicine, using techniques well known to the skilled in the art, in order to obtain amphidiploids or,
3. crossing between individuals of different species having a different chromosome number (e.g. *N. tabacum*×*N. trigonophylla*) followed by embryo culture methods and poliploids induction by treating with the mutagen colchicine, using techniques well known to the skilled in the art, in order to obtain amphidiploids.

As indicated above, when there is no induction of diploidisation, as in the cases 1 and 2, the seeds will be mutagenised by chemical and/or physical techniques, when mutation of the chromosome number is induced by diploidisation, as in cases 2 and 3, the selection may be carried out on said mutated seeds so produced or on said seeds further mutagenised by chemical and/or physical techniques. Standard mutation techniques known to the skilled person may be used, such as, by way of example, the treatment of the seed with Ethyl Methane Sulfonate (EMS) (e.g. in aqueous solution at a 0.5% concentration) and living EMS in contact with the seed for variable times e.g. as indicated in example 1, or, as already said with colchicine, so to induce poliploidisation, by X or Gamma radiations performed in suitable fields or, anyhow, following any protocol available in literature used for plant mutagenesis and for performing large scale screenings. The so treated seeds will be allowed to germinate and the plants of the $M_2$ generation will be selected on the basis of the following characteristics: inflorescence shape, number of capsules, number of seeds per capsule, seed dimensions, leaf shape, dimensions of the root apparatus, bearing of the leaf, etc.

According to the present invention, plants having the following characteristics will be selected: plant height 80-120 cm, leaf with thin lamina and straight bearing, compact inflorescence, number of flowers higher than 100, number of capsules higher than 100, number of seeds per capsule higher than 5000, lignified and strong stalk, deep roots.

The quantity of seeds produced by the selected plants will be than verified in open field and only the plants producing at least 20 quintals of seed/hectare at a seeding density of about from 125,000 to 250,000 plants/hectare will be selected.

By chemical and physical mutagenesis and by somatic mutagenesis, mutants of different classes are obtained, hence increasing the probability of finding the desired variants. As an example, a mutant with a lanceolate leaf having an erect bearing allows the increase of the seeding density without compromising the light reception that is important for the photosynthetic activity and hence to increase the seed production per ha. By way of example, a mutant having a deeper root apparatus allows a better anchorage and nourishment of the plant. As an example, a mutant with a compact inflorescence and a higher number of capsules allows to increase the quantity of seed produced by every single plant.

The present invention encompasses the thus obtained and selected plants producing a seed quantity higher or equal to 20 quintals/hectare. The plants of the present invention are modified in order to produce a seed quantity up to 90 quintals per cultivated hectare, hence 20, 30, 40, 50, 60, 70, 80, 90 quintals per cultivated hectare against the 10-12 normally produced by the tobacco plants selected for the leaf production.

The plants of the invention may be obtained also by induction of somatoclonal variants, wherein the above indicated seeds may be treated with sodium hypochlorite and then with 70% ethanol, from the plants germinated from said seeds leaf parts are taken and the formation of calluses is induce and reproduced for variable times in vitro is hence induced from said parts. From said calluses plants having variable characteristics such as: inflorescence shape, number of capsules, number of seeds per capsule, seeds dimensions, leaf shape, dimensions of the root apparatus, leaf bearing, seed production, oil content of the seed, fatty acid composition of the oil, protein content of the seed etc. regenerate, said plant being selectable on the basis of the above mentioned parameters.

The plants of the invention may further be selected for the presence of characteristics such as: percentage of oil content of the seed, fatty acid composition of the oil, protein content of the seed, etc.

The above described plants may further be modified by recombinant DNA techniques in order to obtain further advantageous characteristics, in case said characteristics were not already present in the selected mutants, such as: increase in the percentage of the oil content of the seed, variable fatty acid composition depending on the uses envisaged for the oil, insects resistance, herbicides resistance, fungi resistance, etc.

For the genetic transformation of the plants of the invention vectors suitable for plant cells transformation may be used as well as expression cassettes allowing the in plant expression of the genes of interest. Depending whether the genes of interest are to be expressed in the green part of the plant (i.e. genes for parasites or herbicides resistance) or in the seeds (e.g. genes involved in the fatty acids metabolism) vectors known in the art, ensuring the expression of said genes in the organs of interest may be selected. Hence, vectors with constitutive promoters known in the state of the art, or with inducible promoters, e.g. by the parasites attack or in the forming capsule may be used. In particular, as the plants of the invention are selected for the high seed production and, being the product of said seed of particular interest, vectors comprising seed specific expression cassettes that will guarantee the expression of the heterologous inserted genes in the seeds of the plant of the invention will be particularly suitable.

For the genetic transformation the *Agrobacterium tumefaciens* or physical DNA transfer systems may be used.

In an embodiment of the invention, it will be particularly advantageous to realise plants presenting not only a high seed productivity but also insect resistance, herbicides resistance, fungi resistance, drought resistance, this will allow to reduce significantly the cultivations inputs, thus increasing the culture productivity and reducing the environmental impact.

In this case vectors comprising the kanamycine resistance gene as marker, regulating regions allowing the constitutive expression (e.g. 35S or the ubiquitin promoter) of the genes of interest such as the cry gene of *Bacillus thuringiensis*, the aroA gene of *Salmonella typhimurium*, the Rpt1 gene of *N. obtusifolia*, may be used. Said genes allow, in the same order, the production of plants resistant respectively, to: insects, herbicides, fungal diseases and may be introduced according to standard gene transfer techniques known to the skilled person.

Resistances can be introduced following one or more transformation events with several vectors or, alternatively, due to the fact that plants may be very easily crossed, the resistances can be introduced singularly in different individuals of the same selected variety and subsequently assembled together in the same individual by crossing.

In this case it will be easy to obtain homozygosis for all the characters by duplication of haploids obtained from in vitro anthers cultures.

The genetic transformation can be carried out in an analogous way for metabolic engineering purposes aimed to the increase of the amount of oil accumulated in the seeds and to the fatty acids metabolic pathway modification. In this case, it is possible to use regulating regions with seed specific activity such as the globulins promoter, and directing the enzymatic proteins to the endoplasmic reticulum where they can be stabilise inserting a specific signal, such as KDEL, or where from there can be translocated to plastids, inserting amino acid specific signals, e.g. the leader sequence of the small RuBisCO subunit.

By way of example, the oil quantity and the fatty acids composition of the same, may be modified by modifying the expression of genes coding for enzymes such as, merely by way of example, acetyl-CoA carboxylase (ACCase), diacylglycerol acyltransferase (DGAT), lysophosphatidate acyl transferase (LPAT), Phosphatidate phosphohydrolase (PA-Pase) acyl protein carrier (ACP), malonyl-CoA:ACP transacylase, ketoacyl-ACP synthase (KAS), ketoacyl-ACP reductase, 3-hydroxyacyl-ACP dehydrase, enoyl-ACP reductase, stearoyl-ACP desaturase, acyl-ACP thioesterase, glycerol-3-phosphateacyltransferase, 1-acyl-sn-glycerol-3-phosphate acyltransferase, cytidine-5-diphosphate-diacylglycerol synthase, phosphatidyl glycerophosphate synthase, phosphatidyl glycerol-3-phosphate phosphatase, FAD1-8 desaturase, phosphatidic acid phosphatase, monogalactosyl diacyl glycerol synthase, digalactosyl diacyl glycerol synthase, sulpho lipid biosynthesis protein, long chain acyl-coA synthase, glycerol-3-phosphate acyltransferase (GPAT), diacylglycerol cho linephospho transferase, phosphatidylinositol synthase, acil-CoA diacylglycerol acyltransferase, acyl-ACP desaturase, lineoyl desaturase, sphingolipid desaturase, oleate 12-desaturase, fatty acid acetylenase, fatty acid epoxygenase, diacylglycerol kinase, cholinephosphate cytidyl transferase, choline kinase, phospholipase, phosphatidylserine decarboxylase, phosphatidylinositol kinase, ketoacyl-CoA synthase, CER transcription factor, oleosin, 3-ketoacyl-CoA thio lase, acyl-CoA dehydrogenase, enoyl-CoA hydratase, acyl-CoA oxidase.

According to the invention, an increase in the total seed oil content can be obtained determining an over expression of the tobacco Acetyl CoA carboxylase or the same enzyme of another species (e.g. rape). As an example, a variation in the fatty acid profile and hence in the iodine number, can be obtained by silencing through the expression of antisense constructs, the gene coding for oleate desaturase of the plastid and of the endoplasmic reticulum. The expression or the silencing of one or more of said genes in the seeds of the plants of the invention, results in the fact that the oil produced by said seeds can be directly used for the production of biodiesel, as it has a iodine number inferior or equal to 120.

The expression of said genes can also affect the percentage of oil in the seed and the plants of the invention can be further selected for the seed's oil content that can be equal to about 38% of the seed weight, the 40%, the 48%, the 52%, the 58% and even the 60%.

The above mentioned genes can be introduced in vectors for the seed specific expression such as the ones described in patent application WO03073839 following the teachings disclosed in said application. The expression vector used for the said embodiment will hence be a vector comprising: a. a promoter of a plant gene specific for the expression in the seed storage organs; b. a DNA sequence coding for the signal sequence of a plant protein capable of direct the product of the gene of interest into the seed storage organs via the endoplasmic reticulum; c. a DNA sequence coding for said gene of interest deprived of the native signal sequence; d. a stop signal. The promoters and the leader sequences may belong, e.g., to the 7S soybean globulin or to the beta conglycinin soybean gene, or to genes coding for tobacco seed storage proteins.

The above mentioned genes can be introduced following one or more transformation event, or by transformation with several vectors, or, alternatively, as plants may be easily crossed, said genes may be introduced singularly in different individuals of the same selected variety and subsequently grouped together in the same individual through crossing.

In this case it will be easy to obtain the homozygosis for all the characters by duplication of haploids obtained by in vitro anther cultures.

TABLE 1

Content in fatty acids of some tobacco varieties selected only after mutagenesis, or engineered and selected in order to change the fatty acids metabolic pathway, and selected for the stability of the character. The table points out the result obtained with mutagenesis and the genetic intervention carried out by introducing some of the listed genes in order to change the acidic composition; the oil of the three last columns has a iodine title suitable for the transformation of said oil into biodiesel.

| Component | PLT 103 | PLT 256 | PLT 318 | PLT 335 |
|---|---|---|---|---|
| Palmitic Acid | 6.31% | 8.26% | 7.15% | 17.20% |
| Palmitoleic Acid | 0.11% | 0.18% | 0.18% | 1.25% |
| Stearic Acid | 2.58% | 5.20% | 8.50% | 12.50% |
| Oleic Acid | 12.62% | 22.58% | 25.56% | 53.27% |
| Linoleic Acid | 77.48 | 58.78% | 52.00% | 6.45% |
| Linolenic Acid | 0.65% | 4.15% | 5.25% | 7.80% |
| Arachidic Acid | 0.13% | 0.85% | 0.80% | 0.85% |
| Eicosanoic Acid | 0.13% | 0.58% | 0.56% | 0.68% |

Object of the invention are also the seeds of the plants as described above, that, being mutant plants' seeds, will be as well mutant and will thus contain DNA modifications that will make them differ form wild type seeds. Moreover, as indicated above, said seeds can have a different chromosome number compared to the parental plants (e.g. poliploids) and in most cases will also be transformed with the above mentioned vectors.

When the transformation is made with vectors expressing genes related to the fatty acids metabolism listed above, said seed will also be characterised in that it contains an oil having a iodine title lower or equal to 120 and an oil percentage comprised between the 38% and the 60% of the seed's total weight.

Object of the present application is also the method for the production of the plant of the invention comprising the following steps:

a) seed produced by starting crossings between individuals of the same species belonging to wild type or selected varieties are subject to mutagenesis;

b) said seeds are allowed to germinate and the plants of the M2-M4 generations are selected according to the following parameters:
  i) presence of characteristics that manifest at the phenotypic level selected in the group comprising height of the plant of 80-120 cm, leaves with thin lamina and straight bearing, compact inflorescence, number of flowers higher than 100, number of capsules higher than 100, number of seed per capsule higher than 5,000, strong and lignified stalk, deep roots;
  ii) stability of the selected character in generations after the M2 generation;
  iii) testing of the hereditability of the selected character;

c) the seeds selected at point b) are allowed to germinate and plants are regenerated starting from the callus obtained from the in vitro induced leaf mesophyll in the presence of phytohormones, the plants maintaining the characters selected at point b) in R0-R2 generations are selected;

d) the plants selected at point c) are seeded in open field and plants producing at least 20 quintals per hectare are selected.

In the method described, the plants obtained at point a) can also be obtained by a') carrying out interspecific crossings in the *Nicotiana* genus, followed by the backcrossing of the F1 or by the induction of amphidiploids by treatment of the vegetative apex with colchicine.

The plants obtained with the above described methods may be submitted to further steps e) and/or f) and to a passage g) as indicated below:

e) genetic transformation of the plants obtained at point a-d or a'-d with vectors comprising expression cassettes expressing in plant genes for insects, herbicides and/or fungal diseases resistance selected in the group comprising the cry gene of *Bacillus thuringiensis*, the aroA gene of *Salmonella typhimurium*, the Rpt1 gene of *N. obtusifolia* and selecting the thus transformed plants in the T0-T4 generations for the for insects, herbicides and/or fungal diseases resistance;

f) genetic transformation of the plants obtained at point a-d or a'-d with one or more vector comprising expression cassettes expressing in seed genes of the fatty acids metabolism selected in the group comprising, acetyl-CoA carboxylase (ACCase), diacyl-glycerol acyltransferase (DGAT), lyso-phosphatidate acyl transferase (LPAT), phosphatidate phosphohydrolase (PAPase) acyl protein carrier (ACP), malonyl-CoA:ACP transacylase, ketoacyl-ACP synthase (KAS), ketoacyl-ACP reductase, 3-hydroxyacyl-ACP dehydrase, enoyl-ACP reductase, stearoyl-ACP desaturase, acyl-ACP thioesterase, glycerol-3-phosphateacyltransferase, 1-acyl-sn-glycerol-3-phosphate acyltransferase, cytidine-5-diphosphate-diacylglycerol synthase, phosphatidyl glycerophosphate synthase, phosphatidyl glycerol-3-phosphate phosphatase, FAD1-8 desaturase, phosphatidic acid phosphatase, monogalactosyl diacyl glycerol synthase, digalactosyl diacyl glycerol synthase, sulfolipid biosynthesis protein, long chain acyl-coA synthase, glycerol-3-phosphate acyltransferase (GPAT), diacylglycerol cho linephospho transferase, phosphatidylinositol synthase, acil-CoA diacylglycerol acyltransferase, acyl-ACP desaturase, lineoyl desaturase, sphingolipid desaturase, oleate 12-desaturase, fatty acid acetylenase, fatty acid epoxygenase, diacylglycerol kinase, cholinephosphate cytidyl transferase, choline kinase, phospholipase, phosphatidylserine decarboxylase, phosphatidylinositol kinase, ketoacyl-CoA synthase, CER transcription factor, oleosin, 3-ketoacyl-CoA thiolase, acyl-CoA dehydrogenase, enoyl-CoA hydratase, acyl-CoA oxidase, followed by selection of the plants in the T0-T4 generations for characteristics such as total oil content of the seed and fatty acid composition of the same;

g) crossing of the materials obtained at points a-f or a'-f and selecting the resulting progenies for characteristics such as: high seed productivity, high oil content in the seed, variable fatty acids oil composition depending on the intended use, insects resistance, herbicides resistance, fungal resistance.

The plants at points comprised between b. and f. may, by way of example, be selected for the presence of characteristics that can be pointed out by chemical analysis such as the total oil content of the seed and/or the content in single acidic components of the seed and/or the protein content of the seed.

A further object of the invention is a method for extracting oil from tobacco seeds wherein the oil yield is equal to values of 70 to 95% of the oil contained in said seeds comprising the following steps:

a) mechanically extracting of said oil by pressing producing oil and a residual oilcake;

b) filtering said oil produced in step a) with paper or cloth filters.

The above indicated method has, surprisingly, a yield higher than 70%, which is a totally unexpected yield after using said pressing methods on seeds as small as the tobacco ones. In the present invention, wherein plants having a high seed production are selected with the aim of increasing the tobacco oil production per plant, the discovery that the pressing method applied onto tobacco seeds has a yield comparable to the yield obtainable on large sized seeds, has extremely advantageous applications.

Besides the lower production costs and the totally unexpected yields given the state of the art, said method allows to extract tobacco oil directly in the sites where it can be used for energetic scopes.

In one embodiment, the seed of the invention can be subject to cold pressing using a screw-press or another kind of press, loaded with the seeds. The press may reach temperatures up to about 60° C. when it is steady operating and the oil pressed from the seed is collected and filtered on paper or with cloth filter-press. Other pressing systems suitable for seeds may be used for pressing tobacco seeds.

In order to further improve the yield of the method of the invention, where the oil productivity from the seed is to be exploited at its maximum, it is possible to perform a further step of c) chemically extracting with solvents the residual oil present into the oilcake obtained at point a).

TABLE 2

Characteristics of the tobacco oil obtained by pressing the seed and filtering. The table points out the higher gross calorific value, the low sulphur content, the low viscosity when compared to other vegetable oils.

| Determination | Result | Mis. Un. | Methods |
| --- | --- | --- | --- |
| Flash point | 236.0 | ° C. | UNI EN ISO 27 19 2005 |
| Sulphur | <0.01 | % m/m | ISO 8754 1992 |
| Ashes | 0.005 | % m/m | EN ISO 6245 2002 |
| Viscosity at 50° C. | 21.630 | mm 2/s | UNI EN ISO 3104 200 |

TABLE 2-continued

Characteristics of the tobacco oil obtained by pressing the seed and filtering. The table points out the higher gross calorific value, the low sulphur content, the low viscosity when compared to other vegetable oils.

| Determination | Result | Mis. Un. | Methods |
| --- | --- | --- | --- |
| Melting point | −18 | ° C. | ISO 3016 1994 |
| Calorific value | 9,670 | Kcal/Kg | ASTM D240-97 |
| Volumic mass at 15° C. | 925.0 | Kg/m3 | UNI EN ISO 3675 2002 |
| Saponification value | 193.6 | mg KOH/g | ASTM D94-02 |

It is also object of the invention the use of the plants of the invention and/or of their seeds for the production of liquid or solid fuels, biodiesel, industrial lubricants, plastic materials such as linoleum, dietary supplements for animal feeds, dietary supplements for human use.

The plants of the invention, in fact, do show characteristics that are extremely advantageous for the production of said products as:

they produce an oil obtained by pressing that is ideal, also without refinement as a simple filtering is sufficient, to be used as combustible oil as it has a clear aspect, a cinematic viscosity at 40° C. of 29.11 mm2/s and at 50° C. of 21.63 mm2/s and a sulphur content lower than the 0.01%, entering in a class with very good physical and thermodynamic characteristics;

they produce an oil, obtained from pressing the seed that, even in the simplest embodiment of the invention, hence without the transformation for the expression of genes of the fatty acids metabolism indicated above, may be used for the production of biodiesel once mixed, e.g., with 25% of palm oil, or with other vegetable oil percentages having a lower iodine title, in order to lower the iodine value under the value 120 and that, in the embodiment comprising the expression of one or more of said genes, with the aim to change the fatty acids metabolism, can be directly used for transforming it in biodiesel, having a iodine number equal to 120, or better equal to 100, or even better, equal to 80;

they produce an oilcake, resultant from the pressing of the seed, having an oil content variable form about 6 to 12% and a protein content of about 35%, which is ideal for the dietary supply of animal feeds given its high content of omega 6 fatty acids (linoleic acid);

they produce an oilcake resultant from the pressing of the seed that, as an alternative to its use as animal feed, may be used as solid combustible in coal or biomass' pellet working plants due to its calorific value higher than 4,950 KCal/kg;

they produce an oil with a flashpoint of 236° C. and a melting point of −18° C. thus being suitable for use as non polluting lubricant, e.g. for chainsaw chains, or as lubricant in general;

they produce an oil that, taking into account its composition abounding in polyunsaturated fatty acids (C18:2, PUFA) that are essential for humans and are hence requested for healthiness scopes (omega 6), may be used as food or as dietary supply for humans;

they produce a residual biomass (leaves, stalks, inflorescences, capsules' coating) after the seed harvest, that may reach values of 100 quintals per hectare or, better, of 200 quintals per hectare or, even better, of 300 quintals per hectare with the possibility of further improving the yield per hectare;

they produce a residual biomass that may be used for the uses normally ascribed to it, such as, e.g., gasification, combustion, pyrolisis, anaerobic digestion, fermentation or steam explosion, thus contributing to ameliorate the economical yield of the culture.

Consequently, object of the invention is the use of the plants of the invention in general for the large-scale production of tobacco seeds.

Object of the invention is the use of the said plants and/or seeds for the production of tobacco oil.

Also object of the invention is the use of the plants and/or the seeds for the preparation of tobacco-oil-based or essentially tobacco-oil-consisting fuels for boilers or diesel engines.

In a particularly advantageous embodiment of the invention, said tobacco oil is obtained with the pressing method of the invention and not by solvent extraction.

The extraction method of the invention, in fact, allows the production of an oil that is directly usable as fuel due to the fact that said oil has a kinematic viscosity of 29.11 mm2/s at 40° C. and of 21.63 mm2/s at 50° C. which allows to nebulise it into burners without the need of a fluidifying pre-heating treatment.

A further object of the invention is the use of the plants and/or the seeds of the invention for the preparation of biodiesel by admixing tobacco's seeds oil with, e.g., 25% of palm oil or with other percentages of plant oils reducing the iodine final title. The production of biodiesel according to the invention may be carried out admixing the tobacco oil extracted with the above described method (pressing) with plant oils capable of lowering its iodine title to a value equal or lower than 120.

Also object of the invention is the use of the plants and/or seeds of the invention for the preparation of tobacco's seeds oil having a iodine title equal or lower than 120 without carrying out any procedure aimed to reduce the iodine title on the oil extracted according to the method of the invention. In this embodiment of the invention, transgenic plants and/or transgenic seeds expressing one or more genes, among the ones listed above, of the fatty acids metabolism according to the invention producing a tobacco oil having a iodine title equal or lower than 120 will be used.

In this case, hence, no refining or treating process of the oil will be carried out after the pressing according to the invention, in order to lower the iodine title of the oil thus obtained. The biodiesel according to the invention may hence have a composition of 100% tobacco oil. The biodiesel will be obtained from the tobacco oil according to the normal transesterification procedures with methanol known to the person skilled in the art.

In an embodiment of the invention the biodiesel will consist entirely of tobacco oil having a iodine title lower than 120, or even equal or lower than 100, or even equal or lower than 80, said oil being transesterificated with methanol according to the methods known to the skilled person.

Object of the invention is also the use of the plants and/or the seeds of the invention for the preparation of solid fuels for coal or biomass pellets functioning plants. In this case the biomass resulting from the cultivation may be used, said biomass having a calorific value higher than 4,200 KCal/kg.

Object of the invention are also the fuels obtainable as indicated above, i.e. fuels comprising the oilcake obtained from tobacco's seeds pressing.

Alternatively, the plants and/or the seeds of the invention, may be used for the preparation of dietary supplements for animal feeds. The oilcake resulting from the pressing of tobacco's seeds according to the invention, has an oil content from about the 6% to about the 12% and a protein content of about the 35% of the oilcake weight and a high omega 6 fatty acids content (linoleic acid) that renders it ideal for said scope. In trials carried out on rearing piglets, the substitution of soybean protein flour with the tobacco oilcake in percentages variable from 3% to 7% in isoproteic diets, did not show significant differences in the animals development.

In a further embodiment of the invention, the plants and/or the seeds of the invention may be used for the preparation of non-polluting lubricants. By way of example, the oil obtained with the method of the invention, from plants producing the seed of the invention having no other modifications besides the mutations for the appearance of the basic character (i.e. the high seed production) already show a flash point of 236° C. and a melting point of −18° C., characteristics that renders it suitable for use even as such as non-polluting lubricant e.g. for chainsaw chains or for engines in general.

In a further embodiment, the plants and/or seeds of the present invention, can be used for the preparation of foods or food supplements for human use.

In this case, the oil obtained by the process of the invention, will be further refined in order to eliminate waxes, gums, complex carbohydrates, phospholipids and de-acidified. Once refined it can be used as such or as dietary supplement for human use. The advantage of said use is given by the richness of said oil in polyunsaturated fatty acids (C18:2, PUFA) that are essential for humans and that are required for health reasons (omega 6).

It is obvious that all the embodiments envisaging the use of tobacco's seeds oil, preferably obtained by pressing, or of oilcake resulting from the seed pressing, can be carried out also on non-mutagenised tobacco plants. The unquestionable advantage of the plants of the invention is obviously given by the high seed production and the resulting higher yield of product obtainable by the plants of the invention and by their seeds compared to the yield obtainable from wild type plants and tobacco seeds planted in a comparable cultivating area and with comparable cultivating methods.

The use of tobacco oil for the preparation of lubricants, of human or animal dietary supplements have never been disclosed in the art. Obviously, also all the embodiments in which an oil having a iodine title equal or lower than 120 extracted by pressing and no further treated have never been described.

The plants of the invention, also show a residual biomass (leaves, stalks, capsules and inflorescences coating) that, after the seed harvest, can reach values between 100 and 300 quintals or more per hectare, the use of the plants of the invention as a biomass source for gasification, combustion, pyrolisis, anaerobic digestion, aerobic digestion, fermentation or steam explosion processes as described in the art in order to further increase the economic yield of the culture, is hence an object of the invention.

Object of the invention are also: a tobacco's seeds oil obtainable from the seeds of the plants of the invention with the extraction method of the invention, a biodiesel obtained by said oil by transesterification, fuels comprising said oil, food supplements for humans deriving from said oil further refined, lubricants comprising said oil, tobacco's seeds oil obtainable from the seeds of the plants of the invention by the extraction method of the invention characterised in that it has a iodine title equal or lower than 120 without the need of admixing it with other oils for lowering said title, biodiesel comprising the said oil having a iodine title equal or lower than 120.

EXAMPLES

Example 1

Chemical Mutagenesis

The seed of the variety selected for the mutants induction by chemical mutagenesis, has been placed in a 100 ml flask in the amount of 20 gr per experiment, corresponding to about 200,000 seeds. 50 ml of deionised water have been added to the flask and the seeds have been rehydrated for 14 hours at 25° C. The water has been than substituted with an 0.5% EMS aqueous solution. The seeds have been shacked using a magnet for a time variable from 0.5 to 5 hours, depending on the variety, that in preliminary trials showed a higher mutation frequency for morphological characters such as height of the plant, seeds dimensions, leaves shape, capsules numbers, seed production per plant etc.

Once the treatment period was ended, the mutagenic solution has been discarded by pouring the seeds in a thin sieve and rinsing them for several minutes under running water. Afterwards, the seeds have been rinsed for 6 times in a flask, by adding 50 ml of water and shaking them for 10 minutes at each rinsing.

The seeds have than been dried on filter paper and have been sent to a specialised firm for pelleting.

The pelleted seeds had a final diameter of 1.2 mm and have been used for direct in field seeding ($M_1$) at a 100,000 plants per hectare density. The $M_1$ generation has been allowed to flower, and has been examined for the possible presence of dominant mutations and, once the seeds were ripe, a capsule per plant has been hand-harvested in order to obtain the mass seed that has been used for the open field seeding of the following year and for the phenotypic screening of the $M_2$ generation. Each mutant of interest has been singularly harvested and controlled in the following generations.

Example 2

Somaclonal Variants Induction

The seed of the variety selected for inducing somatoclonal variants has been sterilised by immersion for 5 minutes in a 20% sodium hypochlorite solution followed by an immersion for 1 minute in 70% ethanol followed by 5 washes in sterile water. The seed has been allowed to germinate in rectangular plastic containers of 10 cm per side and of 12 cm of height containing agarised MS medium. From the fully developed plants, parts of 0.5 cm per side of leaf have been cut and placed in Petri discs with MS1 (MS+1 mg/lt 2,4-D) medium in order to induce the formation of the callus. Also individuals $F_1$ obtained from interspecific crossings have been used. The callus collected from leaf discs has been placed in liquid MS1 medium in 250 ml flasks containing 50 ml of medium and shacked at 80 rpm on a rotating plate maintained at 28° C. with a 16 hours photoperiod.

The callus has been maintained in liquid culture for several generations renewing the culture every 20 days and inoculating a new 50 ml liquid media flask with 2.5 ml of the preceding culture. At each generation a part of the callus was distributed on Petri dishes containing agarised MS2 (MS+1 mg/l NAA+1,5 mg/l Kinetin) medium in order to induce the formation of sprouts that, once reached 2 cm of length were transferred on MS3 (MS+1 mg/l IBA) medium to root and for the subsequent transfer in pot in a greenhouse. The obtained variants were screened in the $R_1$ and $R_2$ generations and concerned the leaves dimensions, the leaves shape, the capsules dimensions, the number of seeds per capsule, the oil content of the seeds, etc.

Example 3

Crossing and Chromosomal Duplication

Many *Nicotiana* species are sexually compatible with *Nicotiana tabacum* and, even if the crossing product is sterile, it is possible to backcross using the parental plants as pollinators or induce the formation of amphidiploids. In this species, the work is facilitated by the fact that it is possible to obtain intergeneric hybrids $F_1$ populations of many thousands of individuals, allowing to perform the improvement program based on amphidiploids. The crossings have been carried out both using parental *Nicotiana* spp. having the same chromosome number (e.g. *N. paniculata*x*N. solanifolia; N. tabacum*x*N. rustica*) or a different chromosome number (eg. *N. tabacum*x*N. paniculata; N. tabacum*x*N. longiflora*). The $F_1$ individuals obtained by some cross combination have been cultivated in greenhouse, in order to verify their phenotypic characteristics and to cross them with both the parental plants, as well as allowed to germinate in vitro and micro propagated. The micro propagated material has been used to carry out chromosome duplication experiments by treatment with colchicine in the sprouts reproduction phase or later after the transplantation in pot and before flowering. The sprouts of the germinated seeds have been cut at the basis and transferred on MS media containing 2 mg/liter of benzylaminopurine (BAP). After about 4-5-weeks the lateral sprouts formed were excised and maintained on the same medium. In order to obtain entire plants the transfer was performed on MS medium without hormones in order to induce roots formation. After few days from the excided sprouts transfer on the rooting medium, a drop of a 0.5% colchicine solution was laid onto the same. Once the plants rooted, they were transferred into pots in a greenhouse and allowed to flower in order to verify their fertility and their capability of forming vital seeds. In some cases, in order to allow the hybridisation between different species, it has been necessary to duplicate the aploids and to perform the hybridisation on autotetraploids.

The materials obtained by the backcrossing generations or by the in vitro propagation followed by the chromosome duplication were screened for their phenotypic characteristics and optionally used in the genetic improvement programs.

The chromosome number control in the stabilised amphidiploids lines has been carried out using the root apex.

Example 4

Genetic Transformation Mediated by *Agrobacterium tumefaciens*

Day 1: a small quantity of *Agrobacterium tumefaciens* of the EHA 105 strain containing the plasmid of interest, collected from a culture on Petri dish with a sterile handle, has been inoculated in 2 ml of sterile LB medium. Subsequently, a leaf of a healthy plant presenting no alterations whatsoever and showing, on the other hand, ideal turgidity conditions, has been collected. The leaf has been briefly rinsed in bi-distilled water in order to eliminate the superficial impurities and dipped in a 20% sodium hypochlorite 0.1% SDS solution for 8 minutes and allowed to dry in a sterile cabinet flux. and all the successive operations have been carried out under sterile conditions. In particular the leaf has been dipped into 95% ethanol and shacked in order to fully wet both sides for about 30-40 sec. The leaf has been than allowed to dry completely.

With an ethanol sterilised punch discs from all the leaf surface have been obtained and have been dropped onto plates containing antibiotics-free MS10; in detail, not more than 30 disks per plate have been placed. Subsequently, 2 ml of LB plus *agrobacterium* (freshly inoculated) have been poured on the plate and the bacterial suspension has been uniformly spread with a gentle rotating movement in order to obtain a homogeneous bacterial distribution onto the discs. The LB in excess has been carefully aspirated with a pipette. A negative control where nothing or mere LB has been added has been carried out.

The plates have hence been incubated for 24-48 hours at 28° C., with constant illumination and the bacterial growth has been pointed out by the appearance of a thin opaque halo diffused onto all the plate.

Day 2: the leaf discs have been carefully transferred on a plate containing MS10+cephotaxime 500 mg/l, and incubated for 6 days at 28° C., in constant lighting. This step determines the *agrobacterium* inactivation.

Day 8: the leaf discs have than been carefully transferred onto MS10+cephotaxime 500 mg/l and Kanamicyne 200 mg/l, and incubated for 14 days at 28° C., in constant lighting. This step determined the selection of the transformed plants since the kanamycine resistance gene is carried by the plasmid inserted in *Agrobacterium*.

Day 22: the leaf discs that have grown in the meantime, thus forming a callus, have been carefully transferred onto MS10+cephotaxime 500 mg/l, kanamycine 200 mg/l and carbenicillin 500 mg/l, and incubated for 6 days. This step determines the elimination of the agrobacteria possibly survived to the preceding antibiotic treatments.

Day 28: the leaf discs have been once more transferred onto MS10+cephotaxime 500 mg/l and kanamycine 200 mg/l, and incubated up to the appearance of sprouts. Once the sprouts presented at least two leaves, they have been separated from the callus mass and transferred onto rooting medium MSO+ cephotaxime 500 mg/l and kanamycine 200 mg/l.

Once the roots appeared, the small plants have been extracted from the plate, freed from the agar residues, gently rinsed in running water and planted in small plastic pots in soil and sand (2:1). The soil has been previously saturated with water, subsequently, the pots have been covered with plastic transparent lids in order to maintain high humidity conditions and have been placed in a growing chamber at 25° C. with a daily lighting period of 16 hours. The transgene presence was screened on all plants collecting a leaf portion (250 mg), extracting the DNA and carrying out a first PCR analysis and than, on positive plants, a Southern analysis in order to verify the number of copies of the transgene.

Example 5

Oil Extraction from the Seed

The tobacco seed produced by certain selected varieties has been used for oil production. In one case the analysed seed has a humidity content of 7.01% and a fatty substances content (extraction with hexane) of 39.4%. The oil extraction has been carried out as a cold extraction, using a screw press mod. Komet (IBG, Germany), manually loaded with tobacco seeds. At steady state the press has reached and maintained a temperature of 60° C. After pressing the oil has been filtered on paper and shows high clearness characteristics. The yield of oil extracted has proven to be of the 81.1% of the total oil contained in the seed. The residual oilcake had a oil content of 0.74% and a protein content of 34.5%.

Example 6

Combustion Tests

The oil coldly extracted and filtered with paper filters as in example 5, has been transesterified with methyl alcohol in presence of NaOH. The oil has been heated up to 55° C. and the methanol-NaOH solution added and mixed for 90 minutes. At the end of this step, after cooling down, the mixture has been allowed to stratify thus dividing the lower glycerol layer from the ester. The ester has been washed two times with water and in the first washing phosphoric acid (2.5 ml/liter) has been added to the water. At the end of the process the oil has been heated under vacuum at 90° C. in order to remove all water residuals and the ester obtained is named with the abbreviation TOE (Tobacco Oil Ester). The trials have been carried out with an indirect injection diesel engine (details: 4 cylinders, rotary injection pump, compression ratio 21.5:1, maximum power 55 kW at 4500 rpm). Prior to the combustion trials, analytic parameters such as viscosity at 50° C. (21.63 mm2/s), melting point (−18° C.), superior calorific value (9,670 KCal/kg), volumic mass at 15° C. (925.0 kg/m3), sulphur (<0.01% m/m), ashes (0.005% m/m) have been verified. During the trial a gas analyzer and an hydraulic dynamometer have been used. The oil ester has been used admixed at 20% with diesel having the following main characteristics in comparison with TEO (indicated in brackets): density 840.8 (886.6), viscosity at 40° C. 2.9 (3.3), sulphur content (mg/kg) 6,750 (6). The test results have not pointed out detectable variations in the engine performance using the two products and showed a more complete combustion that resulted in a higher thermal efficiency when the diesel was added up with TEO. The maximum power increase has been observed at 2,200 rpm with a 3.5% increase in comparison with pure diesel (29.86 kW against 28.85 kW). The produced CO is lower in the mixture in comparison to the sole diesel and also the sulphur content is lower, which determines a decrease in the $SO_2$ emission (up to the 40%).

Example 7

Animal Feeding Trials

The oilcake obtained from the tobacco's seeds pressing has been analysed in order to evaluate its suitability for using as a protein dietary supplement in animal feeds.

The analytical data of the oilcake resulting from the pressing point out a fatty substances content of the 10.74%, a protein content of 34.5% and a humidity and volatile substances of 5.97%. The total aminoacids after the sample hydrolyisis are: aspartic acid 2.40%, threonine 1.06%, serine 1.17%, glutamic acid 5.53%, proline 0.83%, glycine 1.29%, alanine 1.18%, valine 1.27%, methionine 0.45%, isoleucine 1.13%, leucine 1.84%, tyrosine 0.97%, phenylalanine 1.43%, histidine 0.72%, lysine 0.72%, arginine 3.36%. Of the total content of fatty substances, the 76.59% consists of linoleic acid that ascribes to the Omega 6 class, that are of particular relevance for animal diet.

The feeding trial has been carried out on piglets having a starting weight of about 8 kg, divided in two groups, each of 20 individuals, a control group fed with a feed having a soybean protein supplement (C), the second one having the same protein amount with respect to the first, wherein soybean was partially substituted with 3% of the tobacco oilcake (T). The animals treated with the oilcake did not show any problems in beginning and continuing for all the test's duration the intake of said feed. The test was constantly monitored and the piglets sowed no gastroenteric trouble. The animals showed a different daily weigh growth (237 gr/head/day with tobacco oilcake, 170 gr/head/day with soybean oilcake), and a final, after 27 days, weigh of 15.2 kg for T and 12.8 for C.

The invention claimed is:

1. A mutagenised tobacco plant characterised in that the plant produces a seed quantity of at least 4000 kilograms per hectare at a seeding density of about 125,000 plants per hectare under growth conditions in which a non-mutagenized tobacco plant would produce a seed quantity of approximately 1200 kilograms per hectare.

2. The plant according to claim 1, wherein said seed quantity is of about 5000 kilograms per hectare at a seeding density of about 125,000 plants per hectare.

3. The plant according to claim 1, characterised in that the plant is further modified in fatty acid metabolism by genetic transformation and produces a seed containing an oil having an iodine title value lower or equal to 120.

4. The plant according to claim 1, characterised in that the plant is further modified in fatty acid metabolism by genetic transformation and produces a seed containing an oil percentage comprised between about 40% to about 60% of the seed.

5. The plant according to claim 3, modified by transformation with one or more expression vectors comprising a seed specific expression cassette comprising, ordered from 5' to 3', a DNA sequence coding for a promoter of a plant gene specific for expression in seed storage organs; a DNA sequence coding for a signal sequence of a plant protein capable of directing said protein to the endoplasmic reticulum (ER); a DNA sequence coding for a signal sequence capable of directing the protein to the plastid or a DNA sequence coding for a signal sequence able to anchor the protein to the ER; a DNA sequence coding for a protein selected from the group consisting of acetyl-CoA carboxylase (ACCase), diacylglycerol acyltransferase (DGAT), lysophosphatidate acyl transferase (LPAT), phosphatidate phosphohydrolase (PA-Pase) acyl protein carrier (ACP), malonyl-CoA:ACP transacylase, ketoacyl-ACP synthase (KAS), ketoacyl-ACP reductase, 3-hydroxyacyl-ACP dehydrase, enoyl-ACP reductase, stearoyl-ACP desaturase, acyl-ACP thioesterase, glycerol-3-phosphateacyltransferase, 1-acyl-sn-glycerol-3-phosphate acyltransferase, cytidine-5-diphosphate-diacylglycerol synthase, phosphatidyl glycerophosphate synthase, phosphatidyl glycerol-3-phosphate phosphatase, FAD1-8 desaturase, phosphatidic acid phosphatase, monogalactosyl diacyl glycerol synthase, digalactosyl diacyl glycerol synthase, sulpholipid biosynthesis protein, long chain acyl-coA synthase, glycerol-3-phosphate acyltransferase (GPAT), diacylglycerol cholinephospho transferase, phosphatidylinositol synthase, acil-CoA diacylglycerol acyltransferase, acyl-ACP desaturase, lineoyl desaturase, sphingolipid desaturase, oleate 12-desaturase, fatty acid acetylenase, fatty acid epoxygenase, diacylglycerol kinase, cholinephosphate cytidyl transferase, choline kinase, phospholipase, phosphatidylserine decarboxylase, phosphatidylinositol kinase, ketoacyl-CoA syntase, CER transcription factor, oleosin, 3-ketoacyl-CoA thiolase, acyl-CoA dehydrogenase, enoyl-CoA hydratase, and acyl-CoA oxidase; and a polyadenylation signal.

6. The plant according to claim 1, characterised in that the plant is further modified by genetic transformation for insect, herbicide and/or fungus resistance.

7. A method for use of the plant according to claim 1, comprising:
a) cultivating the plant; and
b) harvesting seeds from the plant, wherein said seeds are used for manufacturing of a product selected from the group consisting of tobacco oil, fuel oils, biodiesel, animal dietary supplements, solid fuels, human dietary supplements, and lubricants.

8. A method for use of the plant according to claim 1, comprising:
a) cultivating the plant; and
b) harvesting biomass from the plant, wherein said biomass are used for biochemical conversion or for thermochemical conversion by direct combustion, carbonisation, pyrolysis, gasification, anaerobic digestion, aerobic digestion, alcoholic fermentation, or steam explosion procedures.

9. A method for production of the plant according to claim 1, comprising:
a) subjecting to mutagenesis seeds produced by initial crossings between individuals of the same species belonging to wild type or to selected varieties;
b) germinating said mutagenised seeds and selecting plants of M2-M4 generations according to the following parameters:
i) presence of one or more phenotypic manifest characteristics selected from the group consisting of: plant height of 80-120 cm, leaves with a thin lamina and upright bearing, compact inflorescence, flowers number higher than 100, capsules number higher than 100, number of seeds per capsule higher than 5,000, lignified and robust stalk, and deep roots;
ii) stability of said selected one or more characteristics in generations following M2; and
iii) verification of heritability of said selected one or more characteristics;
c) germinating seeds selected in b) and regenerating plants starting from leaf mesophyll callus induced in vitro in the presence of phytohormones and selecting plants maintaining said selected one or more characteristics in R0-R2 generations;
d) seeding in open field plants selected in c) and further selecting plants producing at least 4000 kilograms of seed per hectare at a seeding density of about 125,000 plants per hectare.

10. A method for production of the plant according to claim 1, comprising:
a') producing mutagenised seeds by carrying out interspecific crossings in the *Nicotiana* genus, followed by backcrossing of the F1 individuals and by amphidiploids induction by treating the vegetative apex of the plants produced by said crossings with colchicine;
b) germinating said mutagenised seeds and selecting plants of M2-M4 generations according to the following parameters:
i) presence of one or more phenotypic manifest characteristics selected from the group consisting of: plant height of 80-120 cm, leaves with a thin lamina and upright bearing, compact inflorescence, flowers number higher than 100, capsules number higher than 100, number of seeds per capsule higher than 5,000, lignified and robust stalk, and deep roots;
ii) stability of said selected one or more characteristics in generations following M2; and
iii) verification of heritability of said selected one or more characteristics;
c) germinating seeds selected in b) and regenerating plants starting from leaf mesophyll callus induced in vitro in the presence of phytohormones and selecting plants maintaining said selected one or more characteristics in R0-R2 generations;

d) seeding in open field plants selected in c) and further selecting plants producing at least 4000 kilograms of seed per hectare at a seeding density of about 125,000 plants per hectare.

11. The method according to claim 9 further comprising:
e) transforming plants obtained in d) with vectors comprising expression cassettes expressing in plant genes for insect, herbicide and/or fungal disease resistance and selecting the thus transformed plants in T0-T4 generations for insect, herbicide and/or fungal disease resistance and/or;
f) transforming the plants obtained in d) with one or more vectors comprising expression cassettes expressing in seed genes of fatty acids metabolism followed by selecting the thus transformed plants in T0-T4 generations for characteristics selected from the groups consisting of total oil content of the seeds and fatty acid composition of the same; and
g) crossing the plants obtained in e) and/or f) and selecting resulting progeny for one or more characteristics selected from the group consisting of: high seed production ability in a quantity higher than 4000 kilograms per hectare, seed oil content higher than the 42%, iodine title in the oil obtained from the seeds of said progeny lower than 120, fatty acids composition of oil contained in said progeny seeds variable with respect to the wild type plant, insect resistance, herbicide resistance, and/or fungal disease resistance.

12. A seed of the plant according to claim 1.

13. A method for use of the seed according to claim 12, comprising extracting oil from the seed, wherein said oil is used for manufacturing of a product selected from the group consisting of tobacco oil, fuel oils, biodiesel, animal dietary food supplements, solid fuels, and dietary food supplements for humans.

14. The plant according to claim 1, wherein said seed quantity is of about 7000 kilograms per hectare at a seeding density of about 125,000 plants per hectare.

15. A method for extraction of oil from tobacco seeds of the plant according to claim 1, comprising:
a) mechanically extracting said oil by pressing with helical press and obtaining oil and a residual oilcake; and
b) filtering said oil extracted in a) with paper or cloth filter.

16. The method according to claim 15 further comprising:
c) chemically extracting by use of solvents residual oil contained in the oilcake obtained in a).

17. The method according to claim 16 further comprising:
d) refining the oil obtained in a) or b), and c).

* * * * *